United States Patent
Carver et al.

(10) Patent No.: US 7,991,113 B2
(45) Date of Patent: *Aug. 2, 2011

(54) RELOCATABLE X-RAY IMAGING SYSTEM AND METHOD FOR INSPECTING COMMERCIAL VEHICLES AND CARGO CONTAINERS

(75) Inventors: James Carver, Cottage Grove, OR (US); Andreas F. Kotowski, Rancho Palos Verdes, CA (US)

(73) Assignee: Rapiscan Security Products, Inc., Torrance, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/822,183

(22) Filed: Jun. 24, 2010

(65) Prior Publication Data

US 2010/0329420 A1 Dec. 30, 2010

Related U.S. Application Data

(63) Continuation of application No. 12/339,481, filed on Dec. 19, 2008, now Pat. No. 7,769,133, which is a continuation of application No. 11/198,919, filed on Aug. 5, 2005, now Pat. No. 7,483,510, which is a continuation of application No. 10/600,629, filed on Jun. 20, 2003, now Pat. No. 6,928,141.

(51) Int. Cl.
*G01N 23/083* (2006.01)
*H05G 1/02* (2006.01)

(52) U.S. Cl. ............................. 378/57; 378/197; 378/198
(58) Field of Classification Search .................... 378/57, 378/196, 197, 198
See application file for complete search history.

(56) References Cited

U.S. PATENT DOCUMENTS

| | | | |
|---|---|---|---|
| 2,831,123 A | 4/1958 | Daly | |
| 3,766,387 A | 10/1973 | Heffan et al. | |
| 3,784,837 A | 1/1974 | Holmstrom | |
| RE28,544 E | 9/1975 | Stein et al. | |
| 4,047,035 A | 9/1977 | Dennhoven et al. | |
| 4,139,771 A | 2/1979 | Dennhoven et al. | |
| 4,210,811 A | 7/1980 | Dennhoven et al. | |
| 4,216,499 A | 8/1980 | Kunze et al. | |
| 4,366,382 A | 12/1982 | Kotowski | |
| 4,430,568 A | 2/1984 | Yoshida et al. | |
| 4,501,011 A * | 2/1985 | Hauck et al. | 378/196 |
| 4,566,113 A | 1/1986 | Donges et al. | |
| 4,599,740 A | 7/1986 | Cable | |
| 4,641,330 A | 2/1987 | Herwig et al. | |
| 4,736,401 A | 4/1988 | Donges et al. | |
| 4,788,704 A | 11/1988 | Donges et al. | |
| 4,825,454 A | 4/1989 | Annis et al. | |
| 4,884,289 A | 11/1989 | Glockmann et al. | |
| 4,979,202 A | 12/1990 | Siczek et al. | |
| 5,022,062 A | 6/1991 | Annis | |
| 5,065,418 A | 11/1991 | Bermbach et al. | |
| 5,091,924 A | 2/1992 | Bermbach et al. | |
| 5,098,640 A | 3/1992 | Gozani et al. | |

(Continued)

*Primary Examiner* — Allen C. Ho
(74) *Attorney, Agent, or Firm* — Novel IP

(57) ABSTRACT

The present specification discloses a readily relocatable X-ray imaging system for inspecting the contents of vehicles and containers, and a method for using the same. The system is relatively small in size, and is used for inspecting commercial vehicles, cargo containers, and other large objects. The X-ray imaging system has a substantially arch-shaped collapsible frame with an X-ray source and detectors disposed thereon. The frame is preferably collapsible via a plurality of hinges and may be deployed into an X-ray imaging position, and collapsed into a transport position.

14 Claims, 9 Drawing Sheets

U.S. PATENT DOCUMENTS

| | | |
|---|---|---|
| 5,179,581 A | 1/1993 | Annis |
| 5,181,234 A | 1/1993 | Smith |
| 5,182,764 A | 1/1993 | Peschmann et al. |
| 5,224,144 A | 6/1993 | Annis |
| 5,237,598 A | 8/1993 | Albert |
| 5,247,561 A | 9/1993 | Kotowski |
| 5,253,283 A | 10/1993 | Annis et al. |
| 5,313,511 A | 5/1994 | Annis et al. |
| 5,367,552 A | 11/1994 | Peschmann |
| 5,379,334 A | 1/1995 | Zimmer et al. |
| 5,493,596 A | 2/1996 | Annis |
| 5,638,420 A | 6/1997 | Armistead |
| 5,642,393 A | 6/1997 | Krug et al. |
| 5,642,394 A | 6/1997 | Rothschild |
| 5,666,393 A | 9/1997 | Annis |
| 5,687,210 A | 11/1997 | Maitrejean et al. |
| 5,692,028 A | 11/1997 | Geus et al. |
| 5,751,837 A | 5/1998 | Watanabe et al. |
| 5,764,683 A | 6/1998 | Swift et al. |
| 5,768,334 A | 6/1998 | Maitrejean et al. |
| 5,787,145 A | 7/1998 | Geus |
| 5,805,660 A | 9/1998 | Perion et al. |
| 5,838,759 A | 11/1998 | Armistead |
| 5,903,623 A | 5/1999 | Swift et al. |
| 5,910,973 A | 6/1999 | Grodzins |
| 5,930,326 A | 7/1999 | Rothschild et al. |
| 5,940,468 A | 8/1999 | Huang et al. |
| 5,974,111 A | 10/1999 | Krug et al. |
| 6,031,890 A | 2/2000 | Bermbach et al. |
| 6,058,158 A | 5/2000 | Eiler |
| 6,067,344 A | 5/2000 | Grodzins et al. |
| 6,081,580 A | 6/2000 | Grodzins et al. |
| 6,094,472 A | 7/2000 | Smith |
| 6,151,381 A | 11/2000 | Grodzins et al. |
| 6,188,747 B1 | 2/2001 | Geus et al. |
| 6,192,101 B1 | 2/2001 | Grodzins |
| 6,192,104 B1 | 2/2001 | Adams |
| 6,195,413 B1 | 2/2001 | Geus et al. |
| 6,198,795 B1 | 3/2001 | Naumann et al. |
| 6,218,943 B1 | 4/2001 | Ellenbogen |
| 6,249,567 B1 | 6/2001 | Rothschild et al. |
| 6,252,929 B1 | 6/2001 | Swift et al. |
| 6,278,115 B1 | 8/2001 | Annis et al. |
| 6,282,260 B1 | 8/2001 | Grodzins |
| 6,292,533 B1 | 9/2001 | Swift et al. |
| 6,301,326 B2 | 10/2001 | Bjorkholm |
| 6,320,933 B1 | 11/2001 | Grodzins et al. |
| 6,356,620 B1 | 3/2002 | Rothschild et al. |
| 6,424,695 B1 | 7/2002 | Grodzins et al. |
| 6,434,219 B1 | 8/2002 | Rothschild et al. |
| 6,435,715 B1 | 8/2002 | Betz et al. |
| 6,442,233 B1 | 8/2002 | Grodzins et al. |
| 6,445,765 B1 | 9/2002 | Frank et al. |
| 6,453,003 B1 | 9/2002 | Springer et al. |
| 6,453,007 B2 | 9/2002 | Adams et al. |
| 6,456,684 B1 | 9/2002 | Mun et al. |
| 6,459,761 B1 | 10/2002 | Grodzins et al. |
| 6,459,764 B1 | 10/2002 | Chalmers et al. |
| 6,473,487 B1 | 10/2002 | Le |
| RE37,899 E | 11/2002 | Grodzins et al. |
| 6,483,894 B2 | 11/2002 | Hartick et al. |
| 6,532,276 B1 | 3/2003 | Hartick et al. |
| 6,542,574 B2 | 4/2003 | Grodzins |
| 6,542,578 B2 | 4/2003 | Ries et al. |
| 6,542,580 B1 | 4/2003 | Carver et al. |
| 6,546,072 B1 | 4/2003 | Chalmers |
| 6,552,346 B2 | 4/2003 | Verbinski et al. |
| 6,563,903 B2 | 5/2003 | Kang et al. |
| 6,580,778 B2 | 6/2003 | Meder |
| 6,584,170 B2 | 6/2003 | Aust et al. |
| 6,597,760 B2 | 7/2003 | Beneke et al. |
| 6,606,516 B2 | 8/2003 | Levine |
| 6,636,581 B2 | 10/2003 | Sorenson |
| 6,653,588 B1 | 11/2003 | Gillard-Hickman |
| 6,658,087 B2 | 12/2003 | Chalmers et al. |
| 6,663,280 B2 | 12/2003 | Doenges |
| 6,665,373 B1 | 12/2003 | Kotowski et al. |
| 6,763,635 B1 | 7/2004 | Lowman |
| 6,785,357 B2 | 8/2004 | Bernardi et al. |
| 6,812,426 B1 | 11/2004 | Kotowski et al. |
| 6,816,571 B2 | 11/2004 | Bijjani et al. |
| 6,837,422 B1 | 1/2005 | Meder |
| 6,839,403 B1 | 1/2005 | Kotowski et al. |
| 6,843,599 B2 | 1/2005 | Le et al. |
| 6,920,197 B2 | 7/2005 | Kang et al. |
| 6,937,692 B2 * | 8/2005 | Johnson et al. ............... 378/57 |
| 7,039,159 B2 | 5/2006 | Muenchau et al. |
| 7,322,745 B2 * | 1/2008 | Agrawal et al. ............... 378/198 |

* cited by examiner

RELOCATABLE X-RAY IMAGING SYSTEM AND METHOD FOR INSPECTING COMMERCIAL VEHICLES AND CARGO CONTAINERS

CROSS REFERENCE

The present application is a continuation of U.S. patent application Ser. No. 12/339,481, filed Dec. 19, 2008 which issued as U.S. Pat. No. 7,769,133, which is a continuation of U.S. patent application Ser. No. 11/198,919, which was filed on Aug. 5, 2005 and issued as U.S. Pat. No. 7,483,510, which is a continuation of U.S. patent application Ser. No. 10/600,629, which was filed on Jun. 20, 2003 and issued as U.S. Pat. No. 6,928,141.

1. FIELD OF THE INVENTION

The field of the invention generally relates to X-ray inspection systems used for security purposes. More particularly, the invention relates to a system and method for inspecting large objects such as commercial vehicles and cargo containers.

2. BACKGROUND OF THE INVENTION

X-ray inspection systems have generally been used to inspect the contents of automobiles, trucks, rail cars, cargo containers, and other vessels of transport. Such systems are generally set up at airports, seaports, building entrances, border crossings, and other places where contraband; weapons, explosives, drugs, or other illegal items are likely to be found in transit. X-ray inspection systems are also often used to verify the contents of containers and vehicles, and to ensure the accuracy of shipping manifests and the like.

X-ray inspection systems for inspecting large objects are generally of the "fixed-site" variety, wherein vehicles or containers are brought to the inspection site to undergo X-ray imaging. Such systems commonly comprise a large inspection tunnel through which vehicles or containers are transported. The vehicles or containers are generally towed through the inspection tunnel, or are transported through the tunnel along a large conveyor mechanism.

As a vehicle or container is transported through the inspection tunnel, an X-ray imaging source generates an X-ray beam toward the vehicle or container. After the X-ray beam passes through, or penetrates, the vehicle or container, a detector receives the beam and produces an output signal representative of the vehicle or container, and of the contents located therein.

In many of these fixed site systems, a plurality of signals representative of individual segments, i.e., successive cross sections or "slices," of the vehicle or container may be transmitted, then summed together, to represent the entire vehicle or container. The output signal, or signals, is then converted into a visual image of the vehicle or container, and of the contents located therein, which is sent to a monitor or viewing screen so that the image may be viewed by an inspection system operator. The system operator may then determine whether any improper items are located, inside the vehicle or container, and whether the vehicle or container should be detained for physical inspection.

While fixed-site X-ray inspection systems have adequately performed in their particular implementations, the need has arisen for an X-ray imaging system that is readily relocatable and/or transportable to meet the needs of a given site or event. This is especially true given the threat that terrorism presents throughout the world, which has led to a greater need to inspect vehicles, containers, and other objects that may be carrying contraband, explosives, or other dangerous or illegal items, in a variety of settings and venues.

Current fixed-site X-ray inspection systems are not suited to meet this need, as they are unable to accommodate areas and events that are not located at, or do not take place near, the inspection sites themselves. Moreover, current fixed-site X-ray inspection systems are unable to deter a large percentage of smugglers who simply move to alternate ports of entry to avoid sites that utilize the fixed-site inspection systems.

In an attempt to resolve these problems, relocatable inspection systems have been developed that can be assembled and used at a variety of locations to inspect large commercial vehicles and cargo containers. In use, these systems may either be stationary, similar to the fixed-site systems described above, or they may move relative to the vehicle or container to be imaged while the vehicle or container remains stationary. In the case of moving inspection systems, existing systems are generally very large and are commonly powered by internal combustion engines. These moving systems may also include linear optical encoders to measure deflection and to compensate for image distortion that occurs while the large system moves over the object to be imaged.

While existing relocatable X-ray inspection systems have been somewhat effective at inspecting vehicles and containers at multiple locations, they have many shortcomings. Specifically, they are generally extremely cumbersome to transport from one location to the next, and they require lengthy disassembling and assembling procedures. Furthermore, these systems generally require powerful machinery to load and unload their components onto and off of multiple transport trucks for relocation. Thus, significant time and expense are required to transport and assemble existing relocatable X-ray imaging systems. As a result, for a given site or event requiring such an inspection system, substantial notice must be given to allow for the time and preparation required to transport and assemble the system. This, in turn, presents significant logistical problems where an event requiring security inspections occurs on short notice.

In light of the above, a need exists for an X-ray imaging system that is used to inspect large trucks and cargo containers, which is readily relocatable, and flexible in terms of on-the-spot reconfiguration, such that a wide variety of site requirements may be met in a short amount of time, and at minimal expense.

3. SUMMARY OF THE INVENTION

The present invention is generally directed to a readily relocatable X-ray imaging system for inspecting the contents of vehicles and containers, and a method for deploying and using the same. In a preferred embodiment, the system is relatively small in size compared to existing X-ray inspection systems, and is used for inspecting commercial vehicles, cargo containers, and other large objects.

In one aspect of the invention, a substantially collapsible frame having an X-ray source and detectors disposed thereon is used for imaging commercial vehicles and large containers. The frame is preferably collapsible via a plurality of hinges and/or slides disposed thereon.

In another aspect of the invention, a method for deploying the frame from a car-carrier type truck or trailer into an X-ray imaging position is described. The truck or trailer preferably includes means for deploying the frame into the imaging position, and for collapsing the frame into a transport position.

In another aspect of the invention, the collapsible. X-ray frame remains stationary during X-ray imaging while a vehicle or container is driven through or towed through an inspection area defined under the frame.

In another aspect of the invention, the collapsible X-ray frame moves relative to a stationary vehicle or container during X-ray imaging. The frame may be self-propelled, self-guided movable along various types of terrain via tires, and/or guided along one or more rails or tracks.

4. BRIEF DESCRIPTION OF THE DRAWINGS

5. DETAILED DESCRIPTION OF THE PREFERRED EMBODIMENTS

The preferred embodiments will now be described. with reference to the figures. To facilitate description, any numeral identifying an element in one figure generally represents the same element when used in any other figure. The configurations shown in the figures are for illustrative purposes only, and are not intended to limit the scope of the invention.

A. Description of System Elements

Figure 1A:
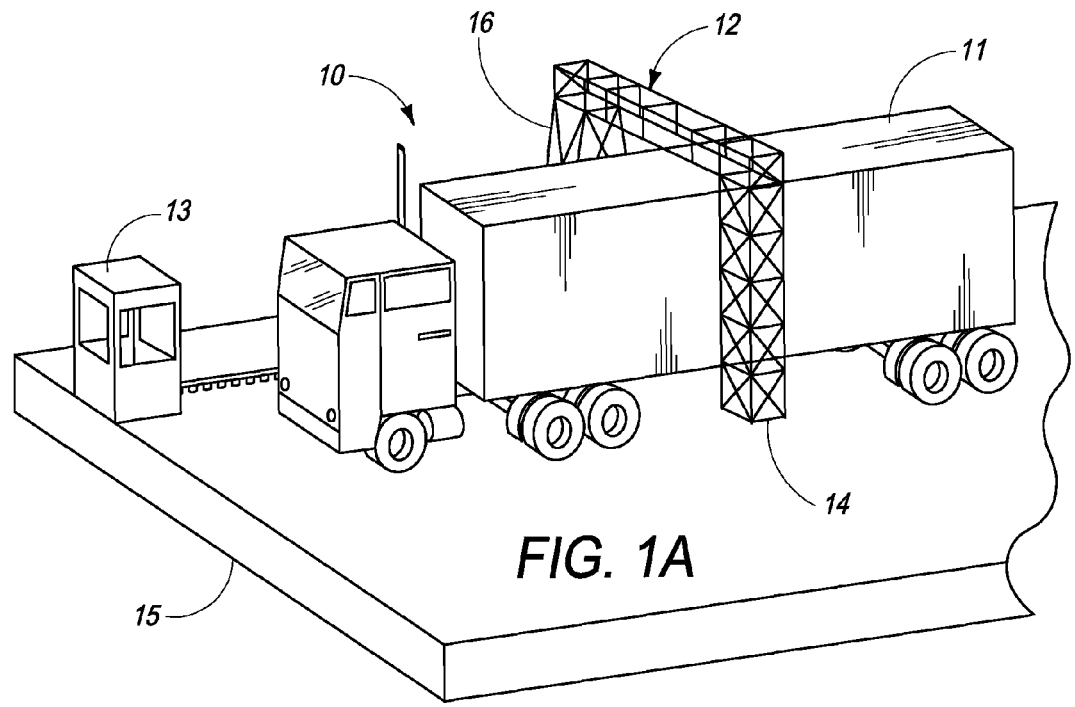
FIG. 1A is a perspective view of the relocatable X-ray inspection system of the current invention set up at an inspection site.
Figure 1B:
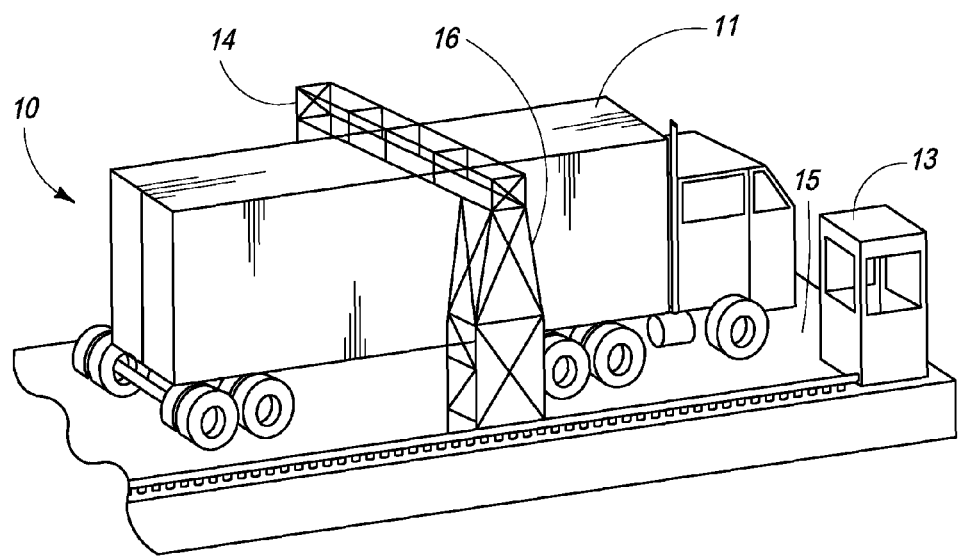
FIG. 1B is an opposite-side perspective view of the relocatable X-ray inspection system of FIG. 1A.

FIGS. 1A and 1B are opposing-side perspective views of a relocatable X-ray inspection system 10. The inspection system 10 may be used for inspecting vehicles, containers, and other objects capable of concealing contraband, weapons, and the like. The inspection system 10 is preferably used for inspecting large commercial trucks and cargo containers, at various sites and events such as border crossings and entrances to government buildings. For ease of description, X-ray imaging of a truck 11 will be described herein, but it is to be understood that the inspection system 10 may also be used to inspect other vehicles, as well as containers and other objects capable of concealing improper items.

FIGS. 1A and 1B show the inspection system 10 set up at an inspection site having an operator cabin 13, with a raisable gate 15 connected thereto, positioned at an entrance and/or exit to the inspection system 10. The operator cabin 13 preferably contains all of the controls necessary for a system operator to manage and oversee the X-ray inspection process. The cabin 13 preferably contains a monitor for displaying X-ray images of objects and materials contained within a truck 11 being inspected, controls for raising and lowering the gate 15, an intercom system for communicating with truck drivers, and other controls for operating the various elements of the X-ray inspection system 10, as further described below.

The inspection system 10 includes a substantially arch-shaped frame 12, which is preferably made from rigid structural steel or any other suitable sturdy material. The frame 12 may be configured as a series of truss beams, or may have any other suitable support configuration. The frame 12 is preferably configured such that it may withstand harsh wind and weather conditions, which may arise during inspection of trucks, such that the frame 12 will not topple over, fall apart, or drift significantly during the inspection process.

Figure 2:
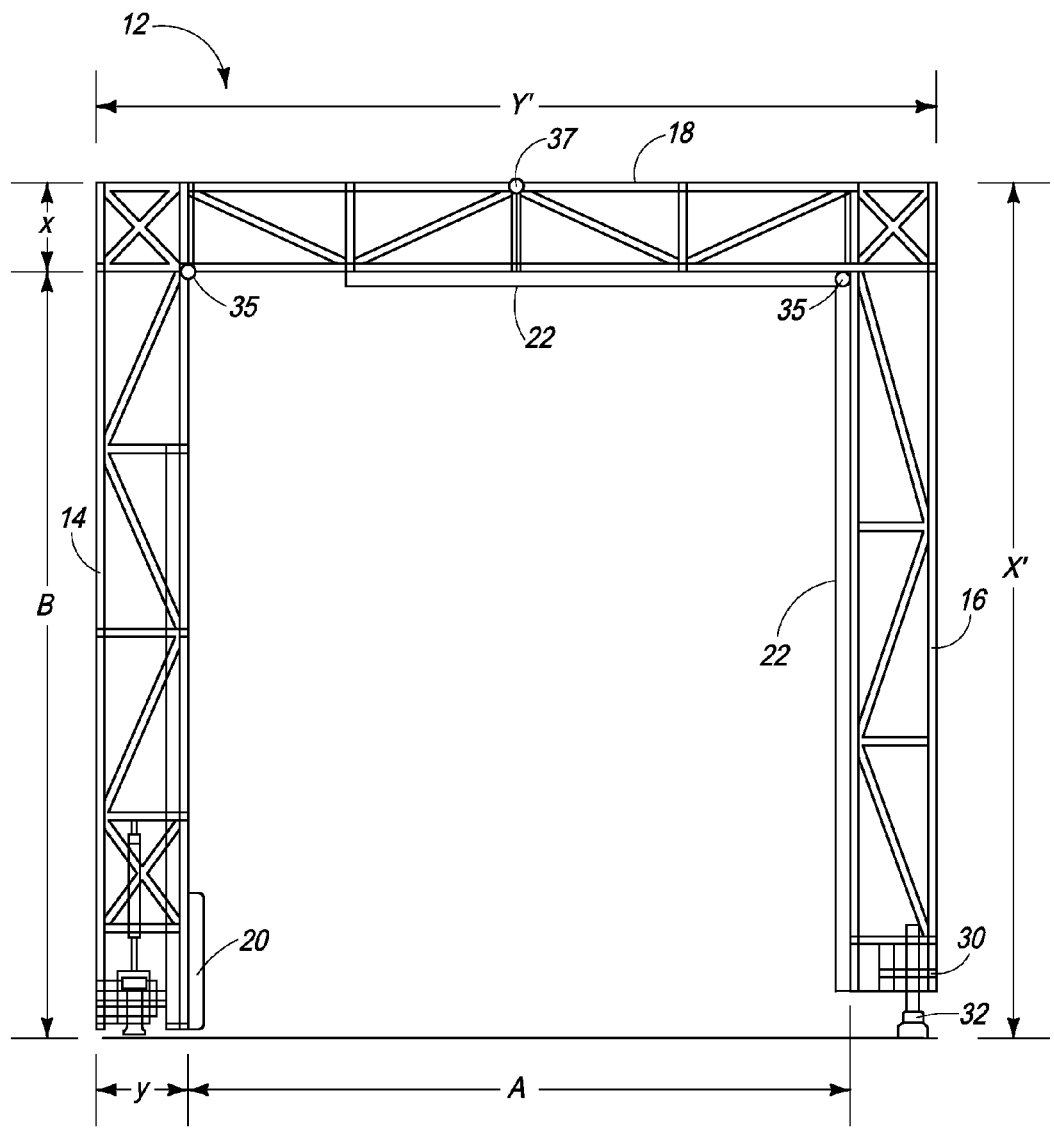
FIG. 2 is a front-sectional view of an X-ray inspection frame according to one embodiment of the current invention.

As shown in FIGS. 1 and 2, the frame 12 preferably comprises a first leg section 14 and a second leg section 16. The first and second leg sections 14, 16 may have feet, wheels, tires, and/or any other support elements located at a base portion thereof for resting on the inspection site surface, which may be the ground, a road, a parking lot, or any other substantially uniform surface, as further described below.

Figure 6:
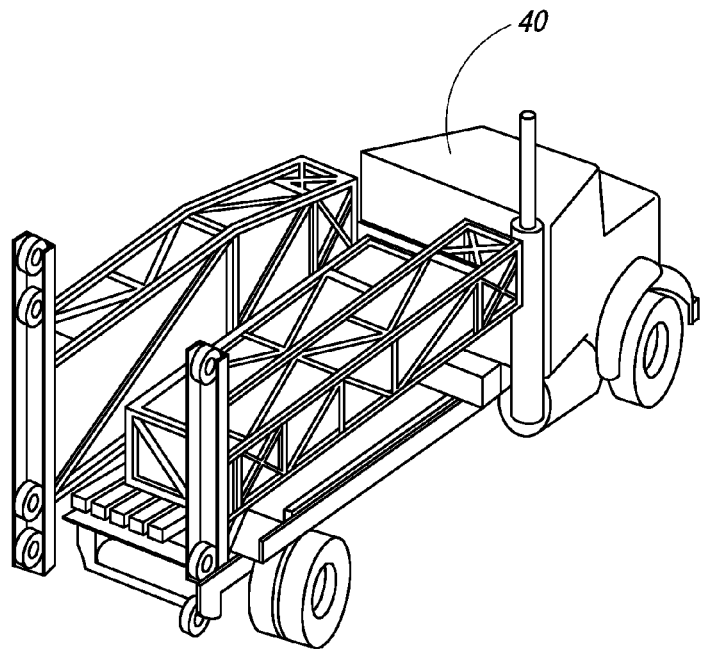
FIG. 6 is a perspective view of the X-ray inspection frame of FIG. 2 in a collapsed position on the bed of a delivery vehicle.

The first and second leg sections 14, 16 are preferably connected to one another by a support beam section 18. The first and second leg sections 14, 16 are preferably pivotally connected to the support beam section 18, by hinges 35 or any other suitable pivoting mechanism, such that the frame 12 may be collapsed, as further described below. Additionally, the support beam section 18 preferably comprises two segments that are pivotally connected to one another at a hinge 37, or other suitable pivoting mechanism, that is located substantially equidistant from the first and second leg sections 14, 16, such that the frame 12 may be collapsed for transport, as illustrated in FIG. 6 and further described below.

The area underneath the support beam section 18 and between the first and second leg sections 14, 16 generally represents an "inspection area" wherein trucks may undergo X-ray imaging. As illustrated in FIG. 2, the inspection area may have a width A 13 to 15 feet, and a height B. For example, and not by way of limitation, width A may be approximately 13 to 15 feet, and height B may be approximately 14 to 16 feet. In this example, inspection system 10 may accommodate vehicles having a width of up to approximately twelve feet, and a height of up to approximately 14 feet.

Still referring to FIG. 2, when the support beam section 18 is in a substantially horizontal imaging position, the support beam section 18 may have a height X and an overall height X'. For example, and not by way of limitation, height X may be approximately 1.5 to 2.5 feet and overall height X' may be approximately 15.5 to 18.5 feet. When the frame 12 is in the imaging position, the first and second leg sections 14, 16 are preferably substantially vertical, and each leg section preferably has a width Y and an overall width Y'. For example, and not by way of limitation, width Y may be approximately 1.5 to 2.5 feet, such that the frame 12 has an overall width Y' of approximately 16 to 20 feet.

At least one of the first and second leg sections 14, 16 preferably includes an X-ray source 20 disposed thereon for generating an X-ray beam toward a truck 11 as it passes through the inspection area. In FIG. 2, the X-ray source 20 is shown disposed on the first leg section 14, but it is to be understood that the X-ray source 20 may be disposed on either, or both, leg sections 14, 16. The X-ray source 20 preferably generates X-ray beams toward detectors 22 disposed on the second leg section 16 and the support beam section 18, such that an entire truck may be imaged, as further described below.

The X-ray source 20 may be any suitable X-ray beam generator, such as a radioisotopic source, an X-ray tube, or an electron. beam accelerator. The X-ray source 20 preferably produces X-ray beams ranging from 300 keV to 10 MeV. Suitable radioisotope sources include Cesium 137 and Cobalt 60. X-ray tubes with accelerating potentials up to 500 keV are generally available. Electron beam accelerator sources such as linear accelerators are generally available with energies from approximately 1 MeV to 10 MeV and higher.

The X-ray source 20 preferably produces a curtain or fan of X-rays so that the truck may be imaged one cross-section or "slice" at a time as it passes through the inspection area. The individual slices may then be summed together to produce an X-ray image of the entire vehicle and its contents. An example of an X-ray inspection system utilizing a fan-shaped X-ray beam is disclosed in U.S. Pat. No. 4,366,382 to Kotowski, which is herein incorporated by reference.

A suitable collimator mechanism may preferably be used to narrow and limit the projected beam into a fan of dimensional, beams necessary to illuminate detectors 22 in the system 10, as further described below. The collimator mechanism also preferably reduces scattered radiation by reducing the total amount of X-rays emitted during truck inspection. As a result, a reduced amount of shielding is required to protect the system operator and the truck drivers and passengers.

In an alternative embodiment, the X-ray beam may be collimated to a flying spot, as opposed to a fan, that moves in a line across one or more detectors (detector configurations are further described below). Such a configuration effectively creates a line camera, which produces images of an object in sections that may be summed together to produce an image of the entire object and its contents. The X-ray beam may alternatively be a pencil-beam, a cone-shaped beam, or any other beam suitable for X-ray imaging. Thus, the fan-shaped beam will be described herein by way of example only.

The radiation produced by the inspection system 10 is preferably maintained at a relatively minimal level compared to the radiation produced by larger fixed-site tunnel systems. This is preferred because the open configuration of the inspection system 10 may allow some scattered radiation to reach a system operator and/or truck passengers, which could endanger their health if the radiation produced is at high concentrations. To further alleviate the danger caused by scattered radiation, radiation shields (not shown in the figures) may be disposed on the first and second leg sections 14, 16 to prevent radiation from escaping the inspection area. As a result, scattered radiation in the inspection system 10 is substantially reduced.

As noted above, detector arrays 22 are preferably disposed on or within the second leg section 16 and the support beam section 18 of the frame 12 for detecting X-ray beams beam after they pass through, or penetrate, a truck 11 or other object being inspected. By placing detectors 22 on both the second leg section 16 and the support beam section 18, an entire truck 11 and its contents may be imaged by the inspection system 10, as illustrated in FIGS. 1A and 1B.

Each detector array preferably comprises a linear array of detectors, such as photodiodes, which absorb the X-ray beams transmitted through the truck 11 being inspected, and convert the absorbed X-ray beams into radiographic signals representative of the truck 11 and of materials contained therein. Alternatively, area detectors, such as scintillating strips or other suitable detectors, may be used to detect the X-ray beams that pass through the truck 11, and to convert the beams into representative radiographic signals.

The signals produced by the detectors may preferably be sent to a. suitable image producing mechanism, such as a system processor, via cables, wires, or other suitable means. Alternatively, the image producing mechanism may receive the detector signals remotely, such that no wires or cables are required. The image producing mechanism preferably converts the detector signals into visual images of the truck 11 and of materials contained therein, which may be viewed on a monitor (or other viewing mechanism) by the system operator.

In a preferred embodiment, the X-ray inspection system 10 is equipped with dual energy imaging capabilities. Dual energy imaging is a process wherein X-ray beams are produced by an X-ray source at multiple radiation energy levels to identify and distinguish between different types of matter. A first detector element is preferably positioned opposite the X-ray source to receive and respond predominantly to X-ray beams in the lower energy range, while the remaining X-ray beams, being generally of higher energy, pass through the first detector element. A second detector element is preferably positioned to receive and respond to the higher energy radiation passing through the first detector element.

A filter element may be interposed between the detector elements to enhance discrimination in the energy response of the respective detector elements. The different detector elements preferably produce separate and simultaneous signals representing patterns of relatively lower and higher energy emergent from a vehicle. Digital data processing and conversion equipment may then use these signals to produce distinctive digital information representative of each of the images inside the vehicle.

For example, color-encoded images may be produced wherein organic, inorganic, and metallic materials located inside a vehicle appear as different colors on a video monitor, such that a system operator may readily distinguish these materials from one another. Thus, by utilizing dual energy imaging in the inspection system 10, the system operator may more easily identify improper materials located inside the vehicle. Dual energy imaging may be particularly effective in the inspection system 10 due to the reduced amount of scattered radiation produced, which may otherwise interfere with optimal dual energy imaging performance.

As an alternative, multiple radiation sources, such as two X-ray sources or isotope sources may be mounted to one of the leg sections. Referring to FIG. 2, the first source 20 may be positioned as shown on leg section 14. In addition, a second radion source may be positioned on frame 12 at another location, such as near the pivot point 35. In this embodiment, a reduced detector array may be used. For example, and again referring to FIG. 2, only the detectors 22 on leg section 16 may be used. This embodiment may provide for the acquisition of time-interleaved images.

The base portion of each of the first and second leg sections 14, 16 may be equipped with feet, wheels, and/or tires, or any other element suitable for providing support and/or motion to the frame 12. The type of element attached to the base portion of each leg section 14, 16 preferably facilitates the method of X-ray inspection being implemented at a given site or event.

Figure 3:
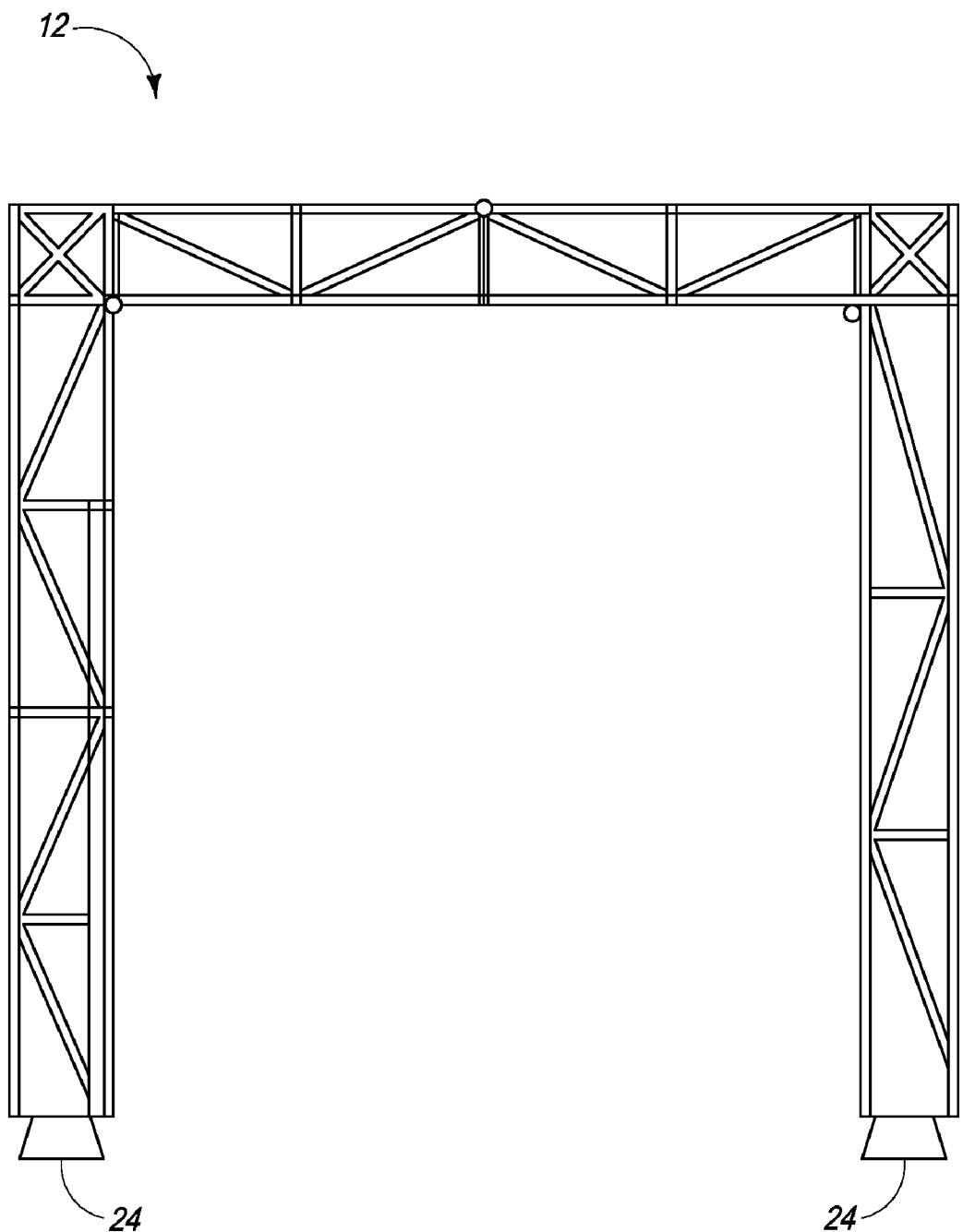
FIG. 3 is a front view of an X-ray inspection frame according to a second embodiment of the current invention.

When an imaging method is employed in which the frame 12 remains stationary during X-ray inspection of a moving object, feet 24 are preferably provided at the base portion of each of the first and second leg sections 14, 16, as illustrated in FIG. 3. The feet 24 provide support to the frame 12, and preferably substantially prevent the frame 12 from sliding or moving along the inspection site surface during X-ray inspection. The feet 24 may be circular, or any other suitable shape, and are preferably made of rubber or any other material that substantially prevents sliding motion of the frame 12 along the site surface. The feet 24 are preferably detachably connected to the frame 12 via bolts, screws, or any other suitable fastening means. Alternatively, an upper portion of each of the feet 24 may be provided with threads, such that the feet 24 may be screwed into corresponding threaded openings in the first and second leg sections 14, 16.

Figure 4A:
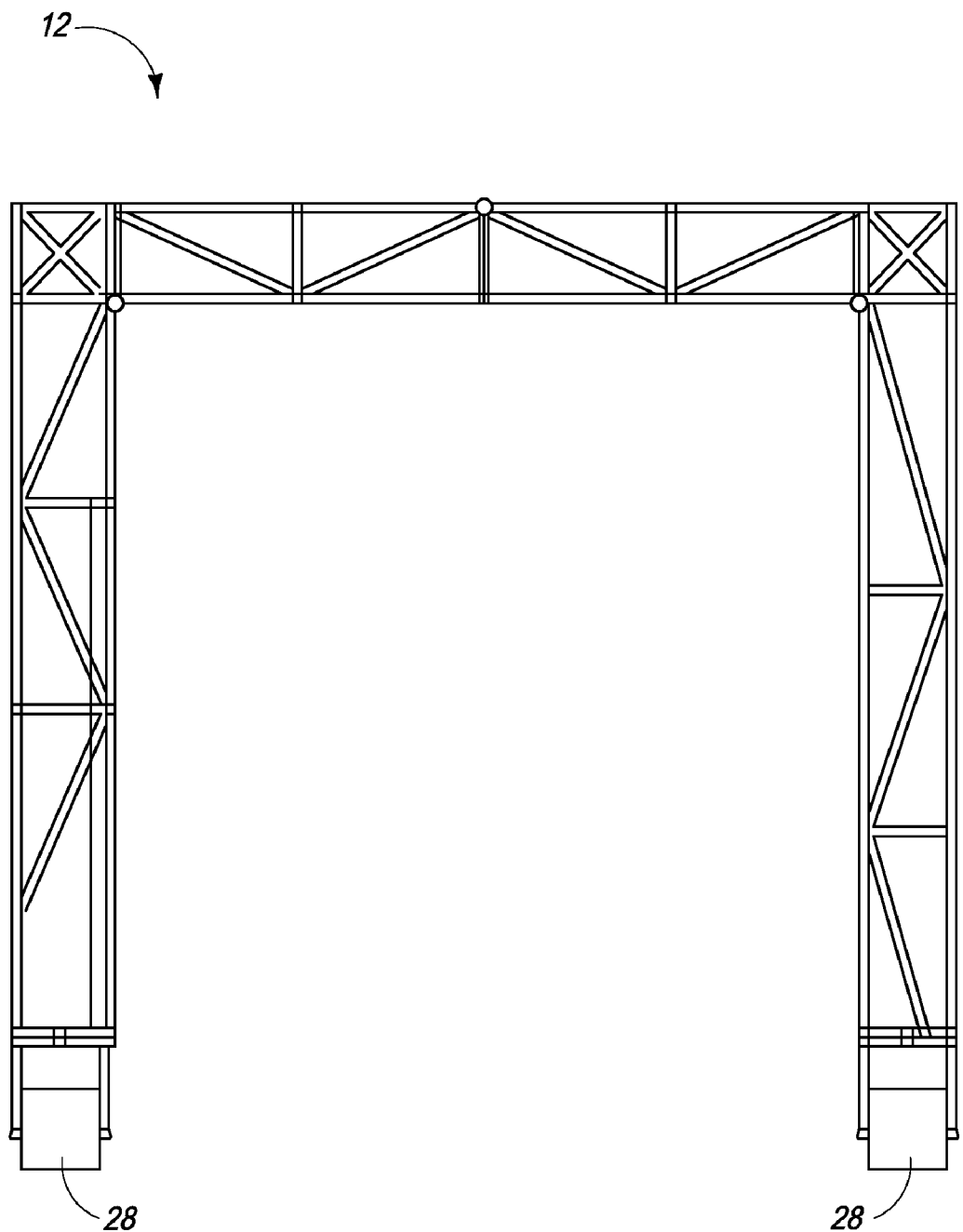
FIG. 4A is a front view of an X-ray inspection frame according to a third embodiment of the current invention.
Figure 4B:
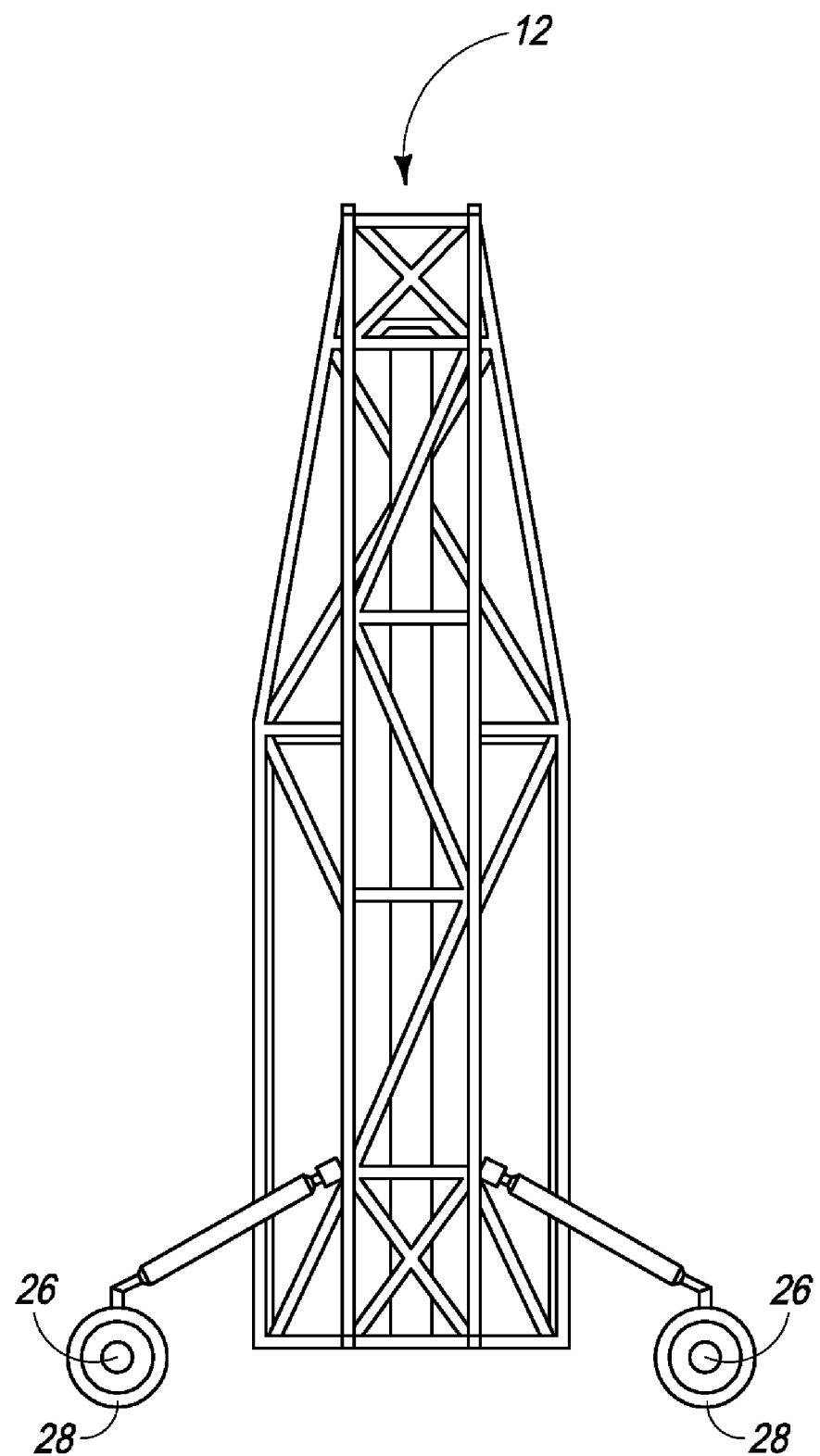
FIG. 4B is a side view of the X-ray inspection frame of FIG. 4A.

FIGS. 4A and 4B illustrated preferred embodiment of the frame 12 wherein the frame 12 may move relative to the object being inspected. One or more wheels 26, which preferably have tires 28 disposed thereon may be rotatably connected to the base portion of each of the first and second leg sections 14, 16. Each leg section preferably has two or more wheels 26 connected thereto to provide balance and symmetry to the frame 12. The wheels 26 are further preferably pivotally attached to the first and second leg sections 14, 16 such that the wheels may pivot to steer the frame 12 during imaging of a stationary object, as further described below.

The tires 28 are preferably made of rubber, or any other suitable material that provides substantially uniform rolling movement to the frame 12 along the site surface. In an alternative embodiment, caterpillar style tracks may be disposed at the base portions of the first and second leg sections 14, 16 to provide rolling movement to the frame 12. Caterpillar style tracks may be particularly effective when the frame 12 performs X-ray inspection on rough or uneven surfaces.

A laser guidance system, or other suitable guidance mechanism, may preferably be used to direct the frame 12 during imaging of an object, as further described below. The laser guidance system may preferably include a suitable laser beam emitter that may be placed on the ground, or at any other suitable location at the inspection site. A target may preferably be positioned at a location where a system operator may aim the laser beam to ensure that the beam is properly aligned, such that the frame 12 may travel toward and away from the beam along a dimension of an object to be imaged, as further described below. The laser guidance system may also include one or more reflectors, which may be positioned to reflect the laser beam toward the frame 12.

The frame 12, in turn, preferably includes one or more sensors for recognizing the laser beam and for producing an output signal indicative of the frame's position or the direction in which the frame 12 is traveling at any given moment. A processor, which may be disposed within the frame 12, in the operator cabin 13, or at any other suitable location, preferably receives the output signal from the frame sensors. The processor may then determine adjustments that must be made to the steering of the frame 12 to ensure that the frame 12 is properly directed along a dimension of an object to be imaged, as further described below.

Figure 5:
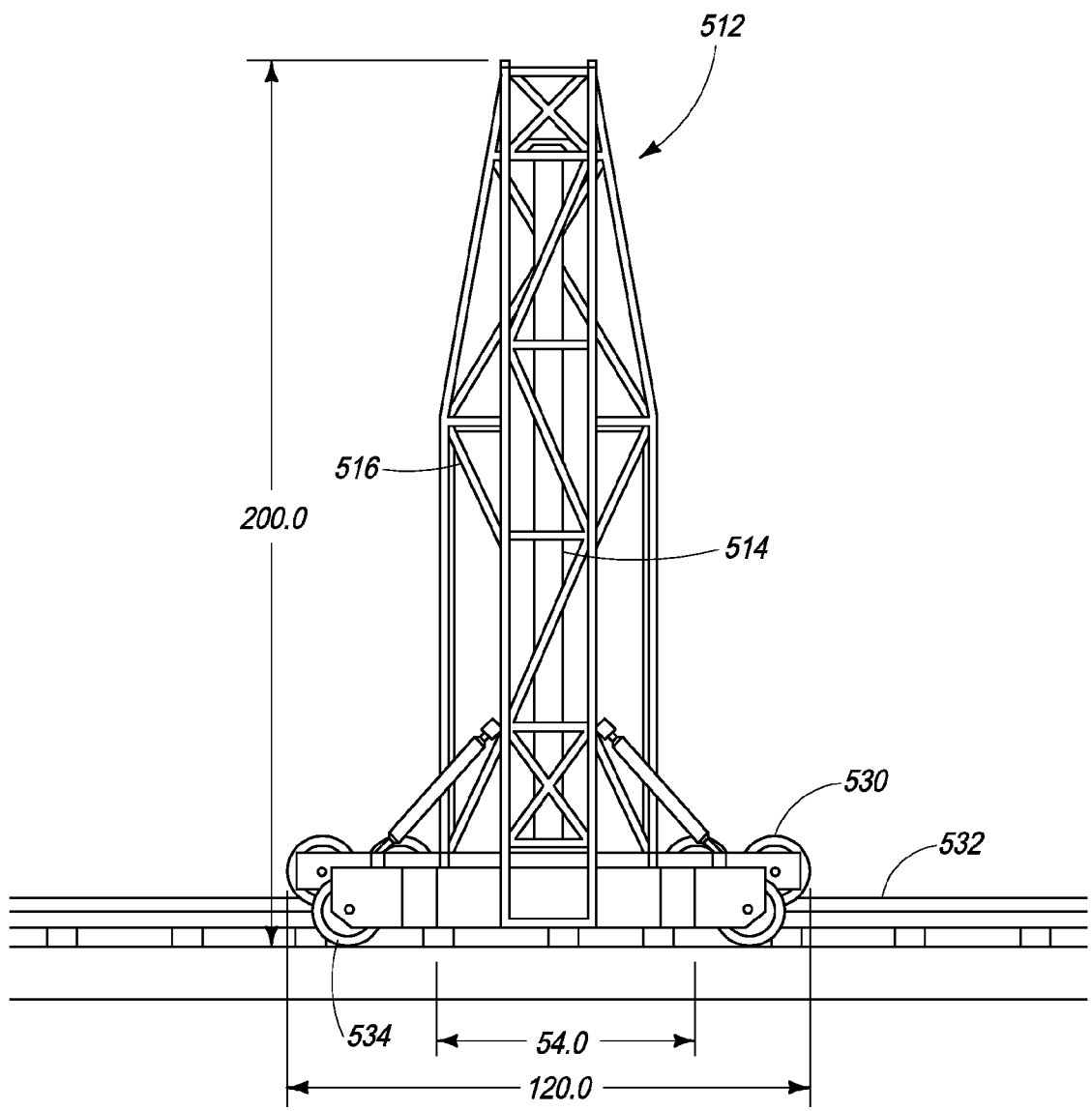
FIG. 5 is a side view of the X-ray inspection frame of FIG. 2 engaging a track.

FIG. 5 illustrates an alternative embodiment wherein the base portion of the second leg section 516 of the frame 512 is equipped with one or more wheels, such as v-wheels 530, which are configured to engage a rail or a track 532. The first leg section 514 may also be equipped with v-wheels for engaging a second track, or may be equipped with one or more conventional wheels 534 for rolling along the inspection site surface, as illustrated. The conventional wheels 34 may have tires disposed thereon, or may be made of a hard plastic, or other suitable material, for rolling along the inspection site surface.

The track 32 is preferably secured to the inspection site surface via wickets, stakes, pins, or any other suitable fastening means. The track may be delivered via the delivery vehicle 40, or may be delivered by a separate vehicle and installed before the frame 12 arrives at the site. Alternatively, the track may be permanently fixed at the site and system 10 may be deployed at that location.

The track 32 may preferably be made of aluminum, or any other material suitable for supporting the frame 12. The v-wheels 30, in turn, may also be made of aluminum, or any other material suitable for rolling along the track 32. During imaging of a truck 11, the frame 12 is preferably guided along the track 32 such that the frame 12 passes over the truck 11 to image the contents located therein, as further described below.

In the embodiments wherein the frame is equipped with wheels and/or tires, the frame 12 preferably includes a self-propelling drive disposed thereon for powering and providing motion to the frame 12. There, self-propelling drive may include one or more synchronous drives, such as electric servo motors or any other suitable source for providing motive power to the frame 12. Servo motors may be used due to the preferred relatively small size of the frame 12, which does not require the power of a large combustion engine, such as those used on existing movable inspection systems, to provide motion thereto.

The servo motors may preferably be activated remotely by controls located inside the operator cabin 13, and/or by controls located on the frame 12 itself. Alternatively, the servo motors may have wires or cables running to the controls in the operator cabin such that the frame 12 may be controlled from within the operator cabin 13.

The servo motors preferably provide motion to the frame 12 in at least two general directions, e.g., forward and backward along a dimension of a truck to be imaged, as further described below. In the embodiment in which the frame 12 is guided along one or more tracks 32, the servo motors preferably provide motion to the frame 12 in two directions along the track(s) 32.

The inspection system 10 may further include one or more generators for providing power to the various components of the inspection system 10. The generator(s) may be located in the operator cabin 13, or at any other suitable location at the inspection site. The generator(s) are preferably electrically connected to the various electrical components in the system 10, such as the imaging equipment and monitors, via wires and/or cables. The servo motors may also be powered and/or recharged by the generator(s).

Figure 7:
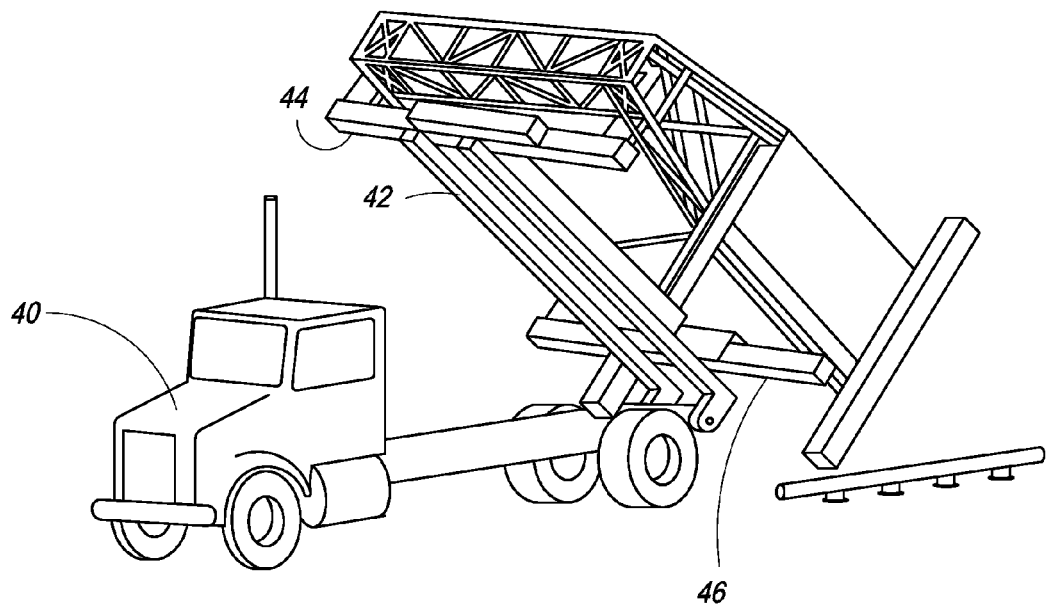
FIG. 7 is an opposite-side perspective view of the X-ray inspection frame of FIG. 6 being deployed from the delivery vehicle onto a track.

The X-ray inspection system 10 may preferably be delivered to an inspection site by a delivery vehicle 40, such as a car-carrier style truck or a platform style tow truck, as illustrated in FIGS. 6 and 7, or by a trailer or other suitable vehicle. The delivery vehicle preferably includes a raisable bed section 42 to which the frame 12 may be attached during transport from one location to another. The raisable bed section 42 preferably has a length to accommodate the height of the frame 12. For example, and not by way of limitation, the length may be from 16 to 20 feet.

The bed section 42 preferably includes a first extendable arm section 44 that may be detachably connected to an upper portion of each of the first and second leg sections 14, 16, and a second extendable arm section 46 that may be detachably connected to a lower portion of each of the first and second leg sections 14, 16. The first and second extendable arm sections 44, 46 are preferably detachably connected to the first and second leg sections 14, 16 via locking levers, or any other suitable locking mechanisms, that may preferably be locked and unlocked manually, and/or via controls located on or inside the delivery vehicle, or at another suitable location.

Figure 8:
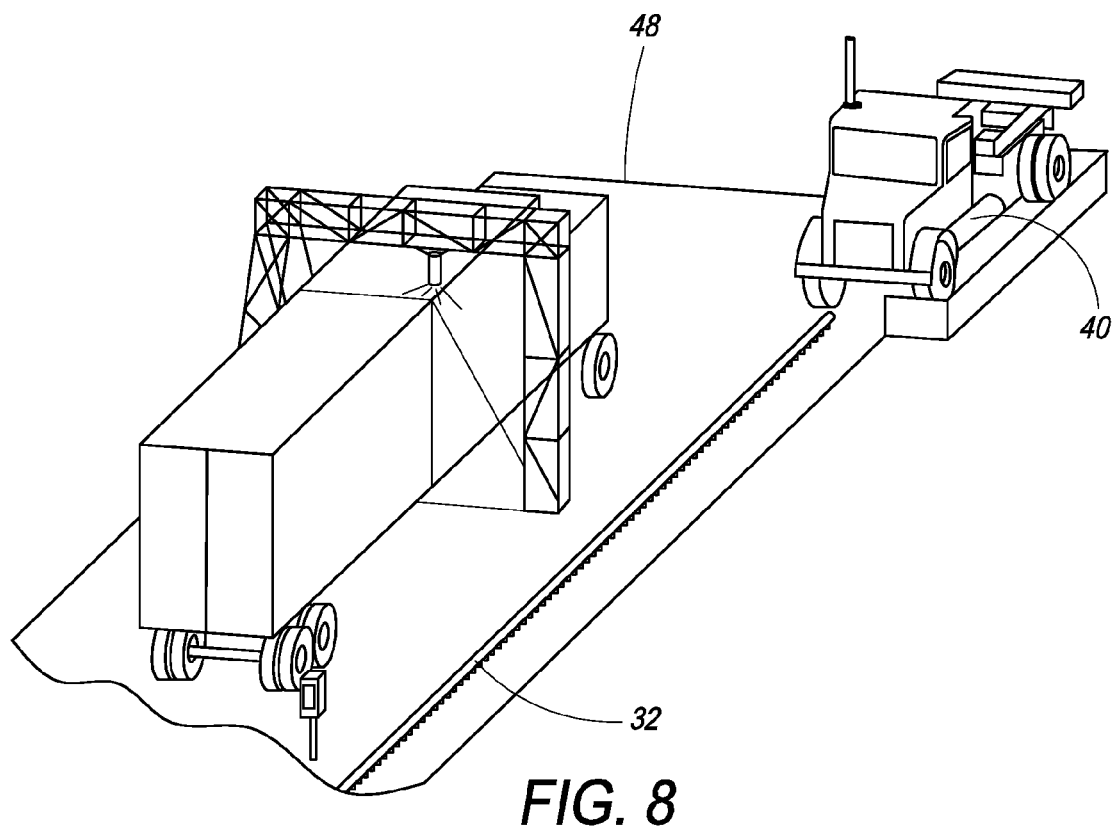
FIG. 8 is a perspective view of the X-ray inspection system of the current invention with a delivery vehicle set up as an operator cabin at the inspection site.

As illustrated in FIG. 8, the delivery vehicle 40 may also be used as an operator cabin. In such an embodiment, the delivery vehicle 40 preferably includes controls therein for operating the X-ray inspection system 10, as further described below. In this embodiment, a raisable gate 48 may preferably be detachably connected to a bumper, or other suitable location, on the delivery vehicle, which the system operator may raise and lower via controls located inside the delivery vehicle 40.

In the embodiment wherein the frame 12 remains stationary during truck inspection, a tow vehicle, or other suitable towing mechanism, may be employed for pulling trucks through the inspection area, as further described below. The tow vehicle may preferably include a winch mechanism having one or more cables that may be attached to the front axle or wheels of the truck to be inspected. Each of the cables preferably includes a clamp, or other suitable attaching means; at a free end thereof, which may be secured to a wheel or axle, or other suitable attachment point on the truck, so that the winch mechanism may pull the truck through the inspection area. In an alternative embodiment, the delivery vehicle 40 may have a towing mechanism located thereon for towing trucks through the inspection area.

B. Description of the Deployment and Relocation Processes

The X-ray inspection system 10 is preferably readily deployable and collapsible, so as to reduce the time and effort involved in moving the system 10 from one inspection site to another. When the delivery vehicle 40 arrives at an inspection site, and at all times during transport, the frame 12 is preferably secured to the bed section 42 of the delivery vehicle 40 in a collapsed transport position, as illustrated in FIG. 6. In the transport position, the first and second leg sections 14, 16 and the support beam section 18 are preferably collapsed against one another via hinges 35, 37, such that they are oriented substantially parallel to one another. As a result, the frame 12 occupies a substantially minimal amount of space on the bed section 42 of the delivery vehicle 40.

Additionally or alternatively, leg sections 14, 16 may comprise telescoping elements that may be retracted for transport and extended for deployment. Also, the leg sections 14, 16 may collapse themselves via hinges positioned along their length. As such, the leg sections 14, 16 themselves may be extended from their retracted and/or collapsed position when frame 12 is being deployed.

To deploy the X-ray frame 12 from the delivery vehicle, the vehicle driver preferably activates the first and second arm sections 44, 46, via controls located inside the vehicle 40, such that the arm sections 44, 46 move outwardly from the delivery vehicle 40 in two directions. As the arm sections 44, 46 extend outwardly, the first and second leg sections 14, 16 of the frame 12, which are secured to the arm sections 44, 46, move away from one another.

The arm sections 44, 46 continue to extend outwardly until the two segments of the support beam section 18 pivot and lock into an imaging position wherein they are substantially linear to one another, and substantially perpendicular to the first and second leg sections 14, 16. In the imaging position, the frame 12 is preferably substantially arch-shaped, as illustrated in FIGS. 2 and 7. The two segments of the support beam section 18 and the first and second leg sections 14, 16 preferably lock into the imaging position via locking levers, or any other suitable locking mechanisms.

After the frame 12 is extended into the imaging position, the vehicle driver preferably raises the bed section 42 of the vehicle 40, as illustrated in FIG. 7, via controls located on or inside the vehicle 40, such that the frame 12 moves into a substantially upright position. In the embodiment wherein the first and second leg sections 14, 16 include v-wheels 30 for engaging a rail or track 32, the vehicle driver preferably aligns the bed section 42 of the vehicle 40 with the track 32 such that the wheels 30 engage the track 32 as the frame 12 is raised into an upright position. In the other described embodiments, the frame is preferably raised until the base portions of the first and second leg sections 14, 16, and/or any tires or feet attached thereto, come into contact with the site surface.

Once the frame 12 is in a substantially upright position on the site surface, the vehicle driver preferably detaches the frame 12 from the vehicle 40 by unlocking the locking levers manually or via controls located on or inside the vehicle. The frame then comes to rest on the site surface in an upright position. In the embodiment where the delivery vehicle 40 is used as an operator cabin, the driver preferably drives the vehicle to a location from where the system operator may manage the inspection process, such as that illustrated in FIG. 8. If the delivery vehicle 40 is not used as an operator cabin, the driver may drive the vehicle 40 away from the inspection area so that it does not interfere with the inspection process.

The delivery vehicle and/or the vehicle driver may further deploy any desired site accessories, such as awnings, signs, turnstiles, radiation shields, the operator cabin 13, and/or any other suitable items, from the delivery vehicle 40. To accomplish this objective, a control cable mechanism, or other suitable deployment mechanism, may be located on the delivery vehicle for deploying the desired accessories, or the accessories may be deployed manually. The deployment mechanism may preferably be operated via controls located on the outside of, or inside the cab of, the delivery vehicle 40. Hydraulic lifts may also be employed for deploying the operator cabin 13. In an alternative embodiment; the operator cabin 13, and any other site accessories, may be delivered by a separate vehicle having a suitable deployment mechanism and/or hydraulic lift(s) located thereon.

After the accessories are deployed, the system operator (who may be the delivery vehicle driver) may arrange the accessories in a suitable manner throughout the inspection site. Radiation shields, for example, may preferably be set up around the inspection area, and/or may be attached to the frame 12, via bolts, screws, hooks, or any other suitable attachment means. Accessories that are too large and/or heavy to be moved manually, such as the operator cabin 13, are preferably deployed directly from the delivery vehicle to their desired locations.

The operator may then connect any electrical cables and/or wires leading from the monitoring equipment, which is preferably located inside the operator cabin 13, to the detector arrays 22 on the X-ray frame 12. The cables and/or wires are preferably used for transmitting signals produced by the detectors to an image processor, or other suitable image-producing mechanism, which provides a visual image of the vehicle and of contents located therein on the monitoring equipment. Alternatively, the detector array may produce output signals that are picked up remotely by the image processor, in which case no cables or wires are required.

When the inspection system 10 is no longer required at a given site, the components of the inspection system 10, and its accessories, may preferably be loaded onto the delivery vehicle(s) in substantially the opposite order in which they were deployed. The vehicle driver may preferably back the delivery vehicle 40 up to the frame 12, and then raise the bed section 42 into a substantially vertical position via controls located on or inside the vehicle 40. The locking levers on the extendable arm sections 44, 46 of the delivery vehicle 40 may then be locked onto the first and second leg sections 14, 16 of the frame, either manually or via controls located on or inside the delivery vehicle 40.

Once the frame 12 is secured to the bed section 42 of the delivery vehicle, the operator, which may or may not be the same individual as the driver, preferably lowers the bed section 42 into a-substantially horizontal position, via controls located on or inside the delivery vehicle 40. The driver may then unlock the locking mechanisms at or near the hinge points 35, 37 on the frame 12, such that the frame 12 may be collapsed into a transport position. The extendable arms 44, 46 may then be retracted via the controls located on or inside the vehicle, which causes the frame to fold up into the transport position. In the transport position, as described above, the first and second leg sections 14, 16 and the support beam section 18 are preferably collapsed against one another such that they are oriented substantially parallel to one another, as illustrated in FIG. 6.

After the frame 12 is secured to the bed section 42 of the delivery vehicle 40 in the transport position, the control cable mechanism and/or hydraulic lift(s) may be used to load the various other site accessories onto the delivery vehicle 40, and/or onto one or more other vehicles. Alternatively, the accessories may be loaded onto the vehicle(s) manually by one or more vehicle drivers and/or system operators. Once all of the system components are loaded onto the vehicle(s), the vehicle(s) may be driven to the next inspection site, or to a storage facility where the inspection equipment may be stored.

C. Description of the Inspection Process

Once the inspection system 10 is deployed and assembled, truck, inspection may begin. To begin the inspection process, a truck is driven to the inspection site, where the truck driver preferably follows directions pertaining to how he/she should proceed, which may be written on signs set up at the site, and/or given verbally by the system operator. An intercom system, similar to that used at a drive-through restaurant, may preferably be set up at the entrance to the inspection site to allow the system operator to communicate instructions, to the truck driver, and to answer any questions posed by the driver.

A gate 15, as shown in FIG. 1, which the operator may raise electronically from inside the operator cabin 13, may be connected to the operator cabin 13 at or near the entrance and/or exit to the inspection system 10. When the system 10 is ready to inspect a truck, i.e., when the previous truck has completed the inspection process, the operator may raise the gate(s) 15 to allow the next truck to enter, and/or the inspected truck to exit, the inspection system 10. The gate(s) 15 may then be lowered by the operator, or lowered automatically once the truck clears the reach of the gate 15, to prevent additional trucks from entering the inspection system 10.

After the driver receives instructions from the operator and/or signs posted at the inspection site, the driver preferably drives the truck to a location near the frame 12, where the truck is preferably aligned with the inspection area of the frame. The site surface may preferably include markings, cones, or other suitable markers to identify the area to which the driver should drive the truck. The truck may then be inspected via any of the methods described below, or via any other suitable inspection process.

When cargo containers are brought to the inspection site to be inspected, the containers are preferably unloaded from a delivery vehicle and placed at or near the inspection area of the X-ray frame 12. The containers may be unloaded manually, by a suitable control cable mechanism, a hydraulic lift, or by any other suitable method. The X-ray frame 12 may then be used to image the containers, via any one of the methods Ascribed below, or via any other suitable inspection method. For ease of illustration, inspection of trucks will be described below, but it is to be understood that other vehicles, containers, and/or any other objects capable of concealing improper items may be inspected by the inspection system 10.

1. Method One—Stationary X-Ray Frame Imaging a Moving Object

In the embodiment illustrated in FIG. 3, the X-ray frame 12 remains stationary while a truck moves through the inspection area of the frame 12 to undergo X-ray inspection. The system operator and/or signs having directions written thereon preferably instruct the truck driver to drive the truck to an area in front of the frame 12. As described above, the site surface may preferably to include markings, cones, or other suitable markers to identify the area to which the driver should drive the truck. The truck may then be pulled through the inspection area by a towing mechanism, or other suitable pulling device, or may be driven through the inspection area by the driver, as further described below.

In the embodiment where the truck is pulled through the inspection area, the truck driver preferably drives the truck to the area indicated in front of the frame 12, then turns the truck off and exits the truck. The driver may then walk along the outside of the inspection system 10 to the opposite side of the X-ray frame 12, and await delivery of the truck after it undergoes the inspection process, in a manner similar to that of a person having bags scanned at an airport.

To facilitate this process, the operator cabin 13 is preferably provided with an intercom system that allows the operator to communicate instructions to the driver regarding where and how the driver should proceed. Warning signs and the like may also preferably be posted at the inspection site informing the driver of where it is safe and unsafe to stand or sit during the inspection process. A seating area may also be provided where drivers may sit during the inspection process.

The system operator and/or other site workers may then attach clamps, or other suitable attachment devices, from the towing mechanism to the front axle, wheels, or other suitable location, on the truck. The winch mechanism may then be activated to tow the truck through the inspection area under the frame 12. The winch mechanism preferably turns at a uniform velocity such that the trucks towed through the inspection area at a substantially constant speed, thereby minimizing/eliminating distortion in the X-ray imaging process.

As the truck begins to pass through the inspection area, an X-ray beam is generated from the X-ray source 20. The X-ray beam may be activated by the operator, or may be activated automatically when the truck reaches a predetermined location under the frame 12. The X-ray beam is preferably generated as soon as the cab section of the truck enters the inspection area, such that the cab section as well as the trailer section may be imaged. Alternatively, the X-ray beam may be generated after the cab section passes through the inspection area, such that only the trailer section undergoes X-ray inspection. In such an embodiment, the operator and/or one or more site workers may preferably physically inspect the cab section to determine whether any improper items are present.

In the embodiment where the driver drives the truck through the inspection area, the X-ray beam is preferably generated after the cab section containing the driver has completely passed through the inspection area, thereby minimizing the radiation to which the driver is exposed. The driver is preferably instructed by the system operator and/or signs posted at the inspection site to drive the vehicle through the inspection area at a substantially uniform velocity, such that distortion in the X-ray imaging process is minimized/eliminated. Signal lights, similar to conventional traffic lights or lights used at car washes, may be included on the frame 12, to notify the driver when he/she should proceed through the inspection area.

In this embodiment, it is preferred that a device equipped with radar, lidar, or other suitable optical distance measuring equipment, be disposed on the X-ray frame 12 for measuring the actual instantaneous position and/or location of the truck as it passes through the inspection area. Such a device allows the system 10 to adjust the X-ray and imaging parameters to accommodate for the potentially non-uniform motion of the truck, and to produce an image with minimal distortion.

Additionally, the radiation levels produced in the embodiment where the driver remains in the truck during the inspection process are preferably maintained within the range of 0.05 micro-Sievert to 0.10 micro-Sievert. This is roughly equivalent to the radiation that a person would be exposed to if he/she were exposed to sunlight for approximately five minutes, and is within ANSI Standard N43.17 (NCRP Report 116), which outlines safe limits of radiation exposure for humans. Thus, the harmful effects of radiation produced in the system 10 are preferably extremely minimal, if existent at all.

In each of the stationary-frame embodiments, as well as the moving-frame embodiments described below, the X-ray beam is preferably produced as a curtain or fan of X-rays, as described above, so that the truck is imaged one cross-section or slice at a time as it passes through the inspection area. A collimator mechanism, as described above, is preferably used to narrow and limit the projected beam into a fan of dimensional beams to illuminate the detectors 22 on the frame 12. The collimator mechanism also limits scattering of the X-ray beam off of the truck onto the detectors, which may otherwise result in a reduction of contrast in the X-ray images produced.

After the fan of X-ray beams passes through the truck, the detectors receive the X-ray beams and produce output signals representative of the individual slices of the truck and of the materials located therein. The output signals are sent to an image processor, which sums the output signals together and converts them into a visual image of the truck and of the contents contained therein. The visual image of the truck and its contents is then sent to a monitor, or other suitable viewing screen, for inspection by the operator.

The operator may then view the images on the monitor to determine whether any improper items are contained within the truck. As explained above, dual energy imaging is preferably used to inspect the truck such that visual images of metallic materials, organic materials, and inorganic materials located inside the truck are readily distinguishable from one another on the monitor. For example, in a preferred dual energy imaging scheme, organic materials, which may be indicative of contraband, may appear as an orange color on the monitor. Metallic materials, conversely, may appear as a blue color. As a result, the system operator is preferably able to readily identify organic materials located inside the truck, which is made up of mainly metallic components.

If the operator determines that one or more improper items might be contained within the truck, the operator may then exit the operator, cabin 13 to physically inspect the truck. Alternatively, one or more truck inspectors may be employed to physically inspect trucks suspected of containing improper items. After physically inspecting the truck, the operator and/or inspectors may detain the driver and the truck if one or more improper items are found inside the truck. If no such items are found, the operator and/or inspectors may then inform the driver that he/she is free to exit the inspection site, and the driver (and any passengers) may then enter the truck and drive away from the inspection site.

Once the previously inspected truck exits the inspection system 10, the operator may then raise the gate 15 on the operator cabin 13 to allow a new truck to enter the inspection system 10 to be inspected. The described inspection process may, then be repeated for the new truck. The entire inspection process is preferably performed in less than two minutes per truck (for trucks not suspected of containing any improper items), more preferably in less than one minute. However, the time of the inspection may vary.

2. Method Two—X-Ray Frame Moving Along a Track to Image a Stationary Object

In the embodiment illustrated in FIGS. 1, 2, and 5, the X-ray frame 12 may move on one or more tracks 32 or rails along a length of a truck while the truck remains stationary. As described above, the delivery vehicle 40 preferably raises the frame 12 such that the v-wheels 32 on the second leg section 16 engage the track(s) 32. The system operator may then activate the servo motors, or other self-propelling drives, on the frame 12 to move the frame into imaging position. In a preferred embodiment, the frame 12 may be positioned adjacent to the operator cabin when the frame 12 is in the imaging position.

Once the frame 12 is in the imaging position, the system operator and/or signs having directions written thereon preferably instruct the truck driver to drive the truck to an area in front of the frame 12. In a preferred embodiment, the driver preferably drives the truck up to the gate 15 on the operator cabin 13, as illustrated in FIGS. 1A and 1B, and then exits the truck so that the truck may be imaged. The driver may then move to an area of the inspection site away from where the X-ray inspection occurs.

To facilitate this process, the operator cabin 13 is preferably provided with an intercom system that allows the operator to communicate instructions to the driver regarding where and how the driver should proceed. Warning signs and the like may also preferably be posted at the inspection site informing the driver of where it is safe and unsafe to stand or sit during the inspection process. A seating area may also be provided where drivers may sit during the inspection process.

Once the driver is safely out of the imaging area, the system operator preferably activates the servo motor(s), or other self-propelling drive, to start the frame 12 in motion along the track 32, such that the frame 12 begins to pass over the truck. Synchronous drives, such as servo motors, are preferably used so that the speed of the frame 12 may be maintained at a substantially constant velocity as the frame 12 passes over the truck, thus reducing/eliminating image distortion that may otherwise occur if the frame 12 velocity varies.

As the frame 12 passes over the truck, an X-ray beam is generated from the X-ray source 20. The X-ray beam may be activated by the operator, or may be activated automatically when the frame 12 reaches a predetermined location on the track 32. The X-ray beam is preferably generated as soon as the frame 12 reaches the cab section of the truck, such that the cab section as well as the trailer section may be imaged. Alternatively, the X-ray beam may be generated after the frame 12 passes over the cab section, such that only the trailer section undergoes X-ray inspection. In such an embodiment, the operator and/or one or more site workers may preferably physically inspect the cab section to determine whether any improper items are present.

The X-ray beam is preferably produced as a curtain or fan of X-rays and detected in the same manner as that described for the stationary-frame embodiments. Additionally, dual energy imaging is preferably used to inspect the truck such that visual images of metallic materials, organic materials, and inorganic materials located inside the truck are readily distinguishable from one another on the monitor, as described above.

Once the frame 512 has passed over the entire length of the truck, the operator preferably deactivates the X-ray source 20, or the X-ray source 20 shuts off automatically when the frame 512 reaches a predetermined location on the track 532. The operator may then view the images on the monitor to determine whether any improper items are contained within the truck.

If the operator determines that one or more improper items might be contained within the truck, the operator and/or the truck inspectors may physically inspect the truck, as described above. After physically inspecting the truck, the operator and/or inspectors may detain the driver and the truck if one or more improper items are found inside the truck. If no such items are found, the, operator then raise the gate 15 on the operator cabin, and the driver (and any passengers) may then enter the truck and drive away from the inspection site.

Once the previously inspected truck exits the inspection site, the operator may activate the servo motors(s) or other synchronous drives on the frame 512 to return the frame 512 along the track(s) 532 to the imaging position, and a new truck may then enter the inspection system 10. The described inspection process may then be repeated for the new truck. The entire inspection process is preferably performed in less than two minutes per truck (for trucks not suspected of containing any improper items), more preferably in less than one minute. However, the time of the inspection may vary.

Alternatively, the frame 512 need not be returned to its original position to perform another scan. This embodiment effectively provides bi-directional scanning or inspection. To this end, once the previously inspected truck exits the inspection area, another truck or other vehicle to be inspected may be positioned in the imaging area with its driver safely away therefrom. The system operator may then activate the servo motors, or other self-propelling driver, to start the frame 512 in motion along track 532 in the opposite direction as the previous inspection. The vehicle may then be inspected in the manner discussed above. This reduces throughput delay due to the frame 512 being returned to a single starting position for each inspection. This also preferably reduces the wear on the components of the system.

3. Method Three—Self-Guided X-Ray Frame, Moving Over a Stationary Object to Image the Object In the embodiment illustrated in FIGS. 4A and 4B, the frame 12 preferably includes a plurality of wheels 26, which preferably, have tires 28 disposed thereon, disposed at a base portion of each of the first and second leg sections 14, 16, as described above. Once the frame 12 is deployed from the delivery vehicle 40, as described above, the X-ray imaging process is performed in essentially the same manner as that described above for the track-guided frame, with the exception that the frame is self-guided and may operate without a track.

In this embodiment, the frame 12 is preferably guided by a suitable guidance mechanism such as an RF guidance system or laser guidance system, or other suitable guidance mechanism. The following discussion pertains to a preferred embodiment involving a laser guidance system. However, it should be noted that other types of guidance systems may be used and the following discussion is applicable to the use of such other guidance systems.

In a preferred embodiment, the system operator or other site worker places or secures a suitable laser beam emitter to the site surface, or other suitable location, and aims the beam at a target positioned in the general path of travel of the frame 12. The operator or site worker may optionally position one or more reflectors at predetermined locations at the inspection site, which may be used to reflect the laser beam toward the target and/or frame 12 during X-ray inspection.

Once a truck arrives at the inspection site, and the driver is safely out of the imaging area, as described above, the system operator preferably activates the laser beam, or other guidance system, and servo motor(s), or other synchronous drives, on the frame 12. The sensors on the frame detect the laser beam and the system processor instructs the frame to follow the laser.

The guidance system may preferably be programmed with tolerance limits within which the frame 12 preferably travels in order to achieve optimal image quality. In this manner, the frame 12 need not travel in a perfectly straight line to produce a useable image, as long as it remains within the tolerance limits. The tolerance limits may vary, but for example and not by way of limitation, the tolerance limits may be less than 6 inches from left to right and/or up and down, but may be greater or lesser depending on the sensitivity of the image-producing equipment. The frame 12 preferably accelerates, decelerates and travels at a pre-determined speed that may be computer controlled or operator controlled. The speed at which the frame 12 travels may vary according to the object being inspected or scanning equipment used in order to preferably provide usable X-ray images.

As the frame 12 passes over the truck, it is guided by the laser which is "tracked" by the sensors on the frame. If the frame moves in any direction up to the designated tolerance limit, the sensors in conjunction with the system processor instruct the frame 12 to move slightly in the opposite or other corrective direction. For example, if the side-to-side tolerance limit is six inches, and the frame 12 moves six inches to the left during the inspection process, a sensor on the frame recognizes that the frame is "off course," and the system processor instructs the frame 1 to move slightly to the right as it progresses over the truck. Furthermore, the speed at which the frame 12 travels may be monitored and varied as desired.

To accomplish this objective, the wheels 26 are preferably pivotally attached to the first and second leg sections 14, 16 such that the wheels may pivot to steer the frame 12 and keep the frame 12 within the tolerance limits of the guidance system. Also, the wheels, tracks or other mechanism used to guide the frame 12 may be independently driven. For example, one track, wheel or other mechanism attached to one frame leg may be temporarily slowed as compared to the other wheel, track or other mechanism attached to the other frame leg such that the frame may be steered from side to side.

As indicated above, the self-guided embodiment of the present invention as discussed above may be used with other guidance systems. For example, the frame 12 may alternatively be guided by a guide wire laid on the ground in the direction of the intended travel path of the frame 12. The guide wire may be secured to the ground by any suitable means such as by stakes or tape. The guidewire system may provide for various motion paths beyond a forward/reverse direction of travel. In another embodiment, the frame 12 may follow a painted, or otherwise marked, line positioned on the ground. Suitable sensor or detectors may be positioned on the frame 12 to gauge the frame's position relative to the line.

As a further alternative, the travel of frame 12 may be controlled optically by a light. In this manner, the frame 12 may move toward the light as its destination. Suitable optical sensors or detectors, e.g., photosensors, mounted on the frame 12 may be used to detect the light. A second light may be used for the reverse direction. In other words, the frame 12 would travel in reverse towards the second light.

In this embodiment, the light source may be located at or near a point towards which the frame 12 is intended to move. The sensors may each photosensors positioned in proximity to each other. The light source may be positioned such that the path of the light may be mid-way between the photosensors. Telescopes or other mechanisms that may focus the light impinging on the photosensors may be used. As the frame 12 travels, it may veer from a straight line or other desired path. As such, certain photosensors in the sensor mounted to the frame 12 may be more illuminated than other of the photosensors in the sensor. Information reflecting the relative illumination of the photosensors may be sent to and processed by the processor described above to cause the frame 12 to change its path of travel, e.g., to bring the frame 12 back to the original straight line or other desired path.

This may occur by the processor sending signals to the drive mechanisms on the legs 14, 16 of the frame 12 such that one of the legs is sped up or the other is slowed or a combination of both. As noted above, legs 14, 16 may be equipped with independent driven wheels, tracks or other mechanisms. The variance between the illumination of the two sides' photocells may reflect how far off course the frame 12 is. As the variance increases, thus indicating that the frame 12 is more off course, the speed difference between the legs 14, 16 may be increased.

Figure 9:
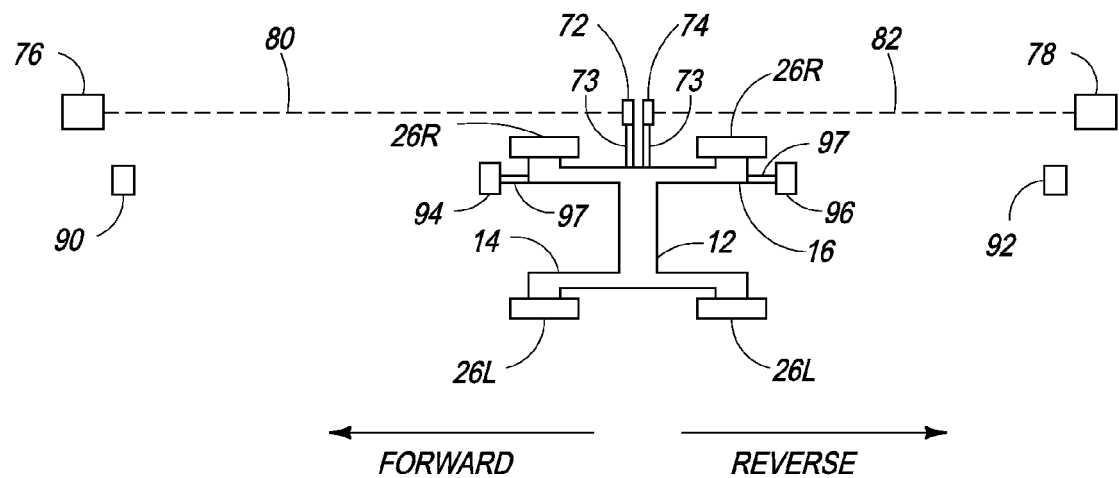
FIG. 9 is a schematic showing an X-ray inspection system using light sensors to guide the movement of the frame of the system.

This embodiment is now further described with reference to FIGS. 9 and 10. FIG. 9 is schematic wherein the frame 12, having legs 14, 16, and having left wheels 26L and right wheels 26R, includes a guidance system. It should be noted that the frame 12 may embody configurations different than that shown in FIG. 9 or different from the frames 12 shown in the other figures discussed above. Accordingly, the guidance system discussed below may be used with frames having various configurations.

Frame 12 may preferably move in the forward and reverse directions per the guidance system. The guidance system may include sensors 72 and 74 that may be mounted to opposite sides of the frame 12 via brackets 73. Other appropriate mounting locations and mounting hardware 73 may be used. While sensors 72, 74 are shown in FIG. 9 on the right side of frame 12, sensors 72, 74 may be mounted elsewhere on the frame, such as on the left side. The guidance system may also include light sources 76 and 78. Light sources 76, 78 may emit a laser light or some other type of light that may be detected by sensors 72, 74. Accordingly, the reference to "light" below is not intended to be limited to some specific type of light.

Light source 76 may emit light generally along the path 80 towards sensor 72. Light source 76 is preferably positioned so that light path 80 generally represents the desired path of forward travel of frame 12. Similarly, light source 78 may emit light generally along path 82 towards sensor 74, and is preferably positioned so that light path 82 generally represents the desired path of reverse travel of frame 12. Light sources 76, 78 may be mounted on a tripod or some other movable structure (not shown) resting on the ground near the inspection sight. Alternatively, light sources 76, 78 may be mounted to an appropriate wall or other stationary structure. It is preferred that sensors 72, 74 are positioned relative to each other so that the light emitted from sources 76, 78 do not shine into each other.

Figure 10:
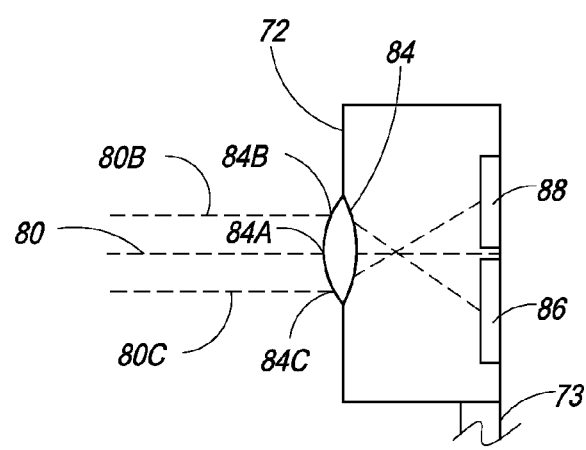
FIG. 10 is a schematic showing light sensors for use in the embodiment of FIG. 9.

Referring to FIG. 10, sensors 72, 74 are now further described. The sensor in FIG. 10 bears the reference numeral 72, but sensor 74 may be similarly configured. As shown, sensor 72 preferably includes lens 84 and photosensors 86 and 88. Lens 84 may comprise any suitable material to accommodate, the type of light being used. While two photosensors 86, 88 are shown, it should be noted that some other number of photosensors, or a photosensor array, may be used.

As mentioned above, light path 80 generally represents the desired path of travel of frame 12. If the frame 12 has been moving along in a relatively straight line along light path 80, light path 80 preferably impinges on the lens 84 at or near its mid-point 84A. This is preferably accomplished by positioning light source 76 relative to the frame 12 and sensor 72 so that the direction of light path 80 does represent the desired path of travel. So when the frame 12 is moving along path 80 and is oriented properly, the direction of the light beam is preferably not significantly altered as it passes through lens 84 and impinges on photosensors 86, 88.

Accordingly, the amount of light received by each of photosensors 86 and 88 from light beam 80 after it passes through lens 84 is preferably the same, about the same, or within some range of tolerance. It should be noted that while light beam 80 is shown in FIG. 10 as a single line, light beam 80 will generally irradiate each of photosensors 86 and 88 to some extent even though these photosensors may not be exactly in the path of the light beam 80. In other words, when the frame 12 is generally on the correct path 80 and is oriented correctly, the light beam 80 covers equal, about equal, or similar enough portions of the photosensors 86, 88.

Signals may be generated reflecting the amount of light energy received by each of the photosensors 86 and 88. These signals may be sent to a processor (not shown in FIG. 10 but described above) for processing. Where the respective signals from photosensors 86, 88 show that the amount of light that they respectively received is the same, about the same, or within a specified tolerable range, the processor need not instruct the drive wheels 26 to alter the path of the frame 12. As such, frame 12 may continue to generally travel in the direction of the desired path 80.

If the frame 12 has strayed from the desired path 80, light beam 80 will impinge on lens 84 at a location other than its mid-point. For example, if the frame has strayed to the left, beam path 80 will impinge on lens 84 at a location 84B as shown in FIG. 10. In this situation, beam path 80 actually impinges on lens 84 from a different path denoted as path 80B. As such, the direction of beam path 80B will be altered as it passes through lens 84 such that beam path 80B will more strongly irradiate photosensor 88 than photosensor 86.

In this situation, the signals reflecting the amount of light received by photosensors 86, 88 will be sufficiently different. These signals may be sent to a processor which may instruct the drive wheels 26 to alter the direction of frame 12 to compensate. To this end, for example, the processor may instruct wheels 26L to speed up, wheels 26R to slow down, or a combination of the two. As the direction of travel of the frame 12 is altered towards the desired path of travel 80, the light emitted from source 76 will eventually impinge on lens 84 at about its midpoint 84A and both photosensors 86, 88 will be illuminated equally, about equally, or within some specified tolerance range. When this occurs, the signals sent to the processor will be the same, about the same or within some specified tolerance range such that further compensation by the wheels 26 may cease.

If the frame 12 has strayed to the right of the desired path 80, beam path 80 will impinge on lens 84 at a location 84C as shown in FIG. 10. In this situation, beam path 80 actually impinges on lens 84 from a different path denoted as path 80C. As such, the direction of beam path 80C will be altered as it passes through lens 84 such that beam path 80C will more strongly irradiate photosensor 86 than photosensor 88.

In this situation, the signals reflecting the amount of light received by photosensors 86, 88 will again be sufficiently different. These signals may be sent to a processor which may instruct the drive wheels 26 to alter the direction of frame 12 to compensate. To this end, for example, the processor may instruct wheels 26R to speed up, wheels 26L to slow down, or a combination of the two. As the direction of travel of the frame 12 is altered towards the desired path of travel 80, the light emitted from source 76 will eventually impinge on lens 84 at about its midpoint MA, and both photosensors 86, 88 will be illuminated equally, about equally, or within some specified tolerance range. When this occurs, the signals sent to the processor will be the same, about the same or within some specified tolerance range such that further compensation by the wheels 26 may cease.

The guidance of frame 12 in a reverse direction may occur in similar fashion. In other words, should the frame 12 proceed on the correct path and be oriented correctly, the light beam 82 from source 78 will impinge the lens 84 at the midpoint and the frame 12 will be instructed to continue travelling on the same course. If the frame 12 strays from the desired path 82, signals may be generated reflecting the different amounts of light received by photosensors 86, 88 which may result in the processor providing appropriate compensating instructions to the wheels 26.

The guidance system of this embodiment may also indicate when the frame 12 has reached the end of the desired length of forward or reverse travel. To this end, the guidance system may include "end of travel" markers 90 and 92 that may be located at the ends of the desired forward and reverse paths of travel. Markers 90, 92 may be positioned relative to the frame 12 in similar fashion to light sources 76, 78. "End of travel" sensors 94 and 96, which correspond to markers 90, 92 respectively, are preferably mounted to frame 12 via brackets 97.

Sensors 94, 96 preferably detect the proper point for the frame 12 to stop. Sensors 94, 96 may be proximity sensors that detect an object, i.e., marker 90 or 92, such as a metal plate or a pole. In one embodiment, the light sources 76, 78 may be mounted to markers 90, 92 respectively. When sensors 94, 96 detect the end of the path of forward or reverse travel, they may generate appropriate signals to a processor to instruct the wheels 26 to stop moving and/or move in the reverse direction.

In general, the guidance system described above may operate as follows. The vehicle to be inspected and/or frame 12 are positioned relative to each other and relative to the light sources 76, 78 and markers 90, 92. As the inspection begins and the frame 12 moves forward, the light source 76 emits light which is received by sensor 72 for appropriate signals to be generated and sent to the processor. Appropriate instructions are then sent to the drive wheels 26. After the inspection has occurred and the frame 12 has reached the end of its desired forward length of travel, sensor 94 sends appropriate signals to the processor to stop the frame 12 and reverse its direction. The reverse movement of frame 12 may then be guided by light source 78 and sensor 74 up until the time that sensor 96 detects that the end of the desired reverse line of travel has been reached. The frame 12 may then be stopped, the inspected vehicle may then exit the inspection area, and another inspection may occur.

The frame 12 is preferably maintained in a relatively stiff configuration such that frame deflection during X-ray inspection is reduced or eliminated, which in turn reduces or eliminates image distortion. To further maintain proper physical alignment, the frame 12 may be equipped with strain gauges that measure strain and/or stress building in the frame 12 before frame deflection actually occurs. The strain gauges may then act to counteract and reduce the strain and/or stress occurring in the frame 12 such that deflection of the frame does not occur.

The use of strain gauges provides an advantage over prior art mobile inspection systems, which generally use linear optical encoders and shaft encoders to measure and compensate for deflection after the deflection has already occurred. Linear optical encoders and shaft encoders, or other suitable compensating equipment, may be used in the inspection system 10, however, if they are more suited to the image producing equipment being used.

The frame 12 may include proximity sensors or physical contact switches to stop the frame 12 if it comes dose to or in contact with another object. Additionally, system 10 may be equipped with cutoff mechanism, e.g., "deadman" switch mechanism that may be used by the operator to stop the frame 12. The cutoff mechanism may also be activated automatically under computer control if certain conditions arise.

After the frame 12 passes over the complete length of the truck being inspected, the X-ray source may be deactivated and the frame 12 may then move in the opposite direction over the truck such that the frame 12 returns to its imaging position. The operator may then view the image of the truck and its contents on the monitor to determine whether any improper items might be present. The operator may then detain the truck and the driver if improper items appear to be present, or inform the driver that he/she is free to leave the inspection site if no improper images appear on the monitor, as described above. Once the previous truck is cleared or detained, and moved away from the inspection area, the next truck may enter the inspection system 10 to undergo X-ray inspection.

Thus while embodiments and applications of the present invention have been shown and described, it would be apparent to one skilled in the art that other modifications are possible without departing from the inventive concepts herein. The invention, therefore, is not to be restricted except in the spirit of the claims that follow.

What is claimed is:

1. A method of deploying a security inspection system from a delivery vehicle to an inspection site, the inspection system including a frame having first and second leg sections pivotally connected to opposite ends of a support beam section, comprising the steps of:
    moving the frame into an X-ray imaging position via a deployment mechanism;
    inclining a bed section of the delivery vehicle until a base portion of at least one of the first and second leg sections contacts a surface of the inspection site or an object located on a surface of the inspection site; and
    detaching the frame from the bed section of the delivery vehicle such that the frame stands in a substantially upright position on the surface of the inspection site.

2. The method of claim 1 wherein the step of moving the frame into an X-ray imaging position comprises moving the first and second leg sections away from one another such that the support beam section pivots into a locked position in which the support beam section is substantially perpendicular to the first and second leg sections.

3. The method of claim 1 wherein the inclining step comprises inclining the bed section until a wheel located on the base portion of at least one of the first and second leg sections engages a track secured to the surface of the inspection site.

4. The method of claim 1 wherein the inclining step comprises inclining the bed section until a plurality of tires located on base portions of the first and second leg sections contact into contact the surface of the inspection site.

5. A method of deploying a security inspection system from a delivery vehicle to an inspection site, the inspection system including a support beam section having a first end and a second end, a first leg section pivotally attached to the first end, and a second leg section pivotally attached to the second end, wherein the support beam section comprises first and second scanner segments pivotally connected to one another, the method comprising the steps of:

activating a deployment mechanism;

moving the first and second leg sections away from one another using the deployment mechanism such that the support beam section pivots into an imaging position in which the first and second scanner segments are locked into place substantially linear to one another, and substantially perpendicular to the first and second leg sections;

inclining a bed section of the delivery vehicle until a base portion of at least one of the first and second leg sections contacts at least one of a surface of the inspection site and an object located on a surface of the inspection site; and detaching the inspection system from the bed section of the delivery vehicle such that the inspection system comes to rest in a substantially upright position on the surface of the inspection site.

6. The method of claim 5 wherein the inclining step comprises inclining the bed section until a wheel located on the base portion of at least one of the first and second leg sections engages a track secured to the surface of the inspection site.

7. The method of claim 5 wherein the inclining step comprises inclining the bed section until a plurality of tires located on the base portions of the first and second leg sections come into contact with the surface of the inspection site.

8. A method of inspecting an object, comprising the steps of:

deploying an X-ray imaging scanner from a delivery vehicle into an imaging position wherein an inspection area is defined by the scanner and wherein the X-ray imaging scanner comprises a support beam having a first end and a second end, a first leg pivotally attached the first end, and a second leg pivotally attached to the second end;

generating an X-ray beam from the scanner into the inspection area toward an object to be imaged;

detecting the X-ray beam after the X-ray beam passes through the object;

producing an output signal representative of the object and contents thereof;

converting the output signal into a visual image of the object and contents thereof;

moving the scanner relative to the object to image the object wherein the step of moving the scanner comprises self-propelling the scanner relative to the object; and regulating a speed and/or alignment with a light source, a light sensor, and a processor.

9. The method of claim 8 wherein the support beam comprises first and second scanner segments pivotally connected to one another.

10. The method of claim 9 further comprising the step of moving the first and second leg sections away from one another using the deployment mechanism such that the support beam section pivots into an imaging position in which the first and second scanner segments are locked into place substantially linear to one another, and substantially perpendicular to the first and second leg sections.

11. The method of claim 10 further comprising the step of inclining a bed section of the delivery vehicle until a base portion of at least one of the first and second leg sections contacts at least one of a surface of the inspection site and an object located on the surface of the inspection site.

12. The method of claim 8 further comprising the step of detaching the X-ray imaging scanner from the bed section of the delivery vehicle such that the X-ray imaging scanner comes to rest in a substantially upright position on the surface of the inspection site.

13. The method of claim 12 wherein the inclining step comprises inclining the bed section until a wheel located on the base portion of at least one of the first and second leg sections engages a track secured to a surface of the inspection site.

14. The method of claim 12 wherein the inclining step comprises inclining the bed section until a plurality of tires located on the base portions of the first and second leg sections come into contact with a surface of the inspection site.

* * * * *